United States Patent

Wichmann

Patent Number: 5,561,150
Date of Patent: Oct. 1, 1996

[54] TRICYCLIC PYRAZOLE DERIVATIVES

[75] Inventor: Jürgen Wichmann, Steinen, Germany

[73] Assignee: Hoffman-La Roche Inc., Nutley, N.J.

[21] Appl. No.: 510,153

[22] Filed: Aug. 2, 1995

[30] Foreign Application Priority Data

Aug. 12, 1994 [CH] Switzerland ............................ 2490/94

[51] Int. Cl.$^6$ ...................... A61K 31/415; C07D 231/54
[52] U.S. Cl. ......................... 514/406; 514/407; 548/359.1
[58] Field of Search .................. 548/359.1; 514/406, 514/407

[56] References Cited

PUBLICATIONS

S. J. Peroutka et al., Brain Research vol. 584, pp. 191–196 (1992).
T. Branchek et al., Molecular Pharmacology vol. 38, pp. 604–609 (1990).
Berendensen & Broekkamp, Eur. J. Pharmacol. vol. 135, pp. 279–287 (1987).

*Primary Examiner*—Patricia L. Morris
*Attorney, Agent, or Firm*—George W. Johnston; Ellen Ciambrone Coletti

[57] ABSTRACT

Compounds of the formula

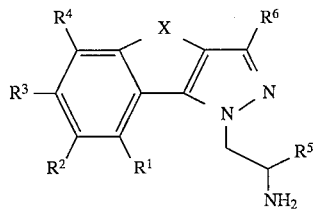

wherein
$R^1$ to $R^4$ each are hydrogen, hydroxy, halogen, lower alkyl, lower alkoxy or phenyl;
$R^5$ is hydrogen or lower alkyl,
$R^6$ is hydrogen, lower alkyl or lower alkoxy;
X is —(CR$^7$R$^8$)$_n$— or —CH=CH—;
$R^7$ and $R^8$ are hydrogen or lower alkyl and
n is 1 or 2,
as well as pharmaceutically acceptable salts of basic compounds of formula I, bind to serotonin receptors, and thus are useful in treating central nervous system disorders.

18 Claims, No Drawings

TRICYCLIC PYRAZOLE DERIVATIVES

BACKGROUND OF THE INVENTION

1. Field of the Invention

The invention relates to tricyclic pyrazole derivatives which bind to serotonin receptors.

SUMMARY OF THE INVENTION

The present invention relates to tricyclic pyrazole derivatives of the formula

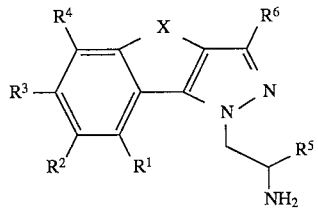

wherein $R^1$ to $R^4$ each are hydrogen, hydroxy, halogen, lower alkyl, lower alkoxy or phenyl;

$R^5$ is hydrogen or lower alkyl, $R^6$ is hydrogen, lower alkyl or lower alkoxy;

X is —$(CR^7R^8)_n$— or —CH═CH—;

$R^7$ and $R^8$ are hydrogen or lower alkyl and n is 1 or 2, as well as pharmaceutically acceptable salts of basic compounds of formula I.

These compounds and salts are novel and have valuable pharmacological properties, such as, the control or prevention of central nervous system disorders.

The compounds of formula I and their pharmaceutically acceptable salts bind to serotonin receptors to simulate action of serotonin. A decrease in serotonin acts to elevate central nervous system depression. Therefore, compounds of the invention, simulating action of serotonin, are useful in treating central nervous system depression. In view of the ability of the compounds of the invention to enhance serotonergic activity, the compounds of the invention may also be useful in treating other disorders mediated by decreased serotonin activity, such as bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressivity, age-related memory disorders and behavioural disorders, addiction, obesity, bulimia and the like, damages of the nervous system by trauma, stroke, neurodegenerative diseases and the like, cardiovascular disorders such as hypertension, thrombosis, stroke and the like and gastrointestinal disorders such as dysfunction of the gastrointestinal tract motility.

Detailed Description of the Invention

The present invention relates to tricyclic pyrazole derivatives of the formula

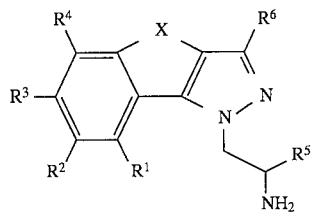

wherein $R^1$ to $R^4$ each are hydrogen, hydroxy, halogen, lower alkyl, lower alkoxy or phenyl;

$R^5$ is hydrogen or lower alkyl, $R^6$ is hydrogen, lower alkyl or lower alkoxy;

X is —$(CR^7R^8)_n$— or —CH═CH—;

$R^7$ and $R^8$ are hydrogen or lower alkyl and n is 1 or 2, as well as pharmaceutically acceptable salts of basic compounds of formula I.

Objects of the present invention are compounds of formula I and pharmaceutically acceptable salts thereof, the manufacture of the compounds of formula I and their salts, medicaments which contain these compounds and salts and the production of these medicaments, as well as the use of compounds of formula I and of pharmaceutically usable salts thereof in the control or prevention of illnesses or in the improvement of health, especially in the control or prevention of central nervous system disorders. In particular, the compounds of formula I are useful in treating depression. The compounds of formula I can also be used for the treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressivity, age-related memory disorders and behavioural disorders, addiction, obesity, bulimia and the like, damages of the nervous system by trauma, stroke, neurodegenerative diseases and the like, cardiovascular disorders such as hypertension, thrombosis, stroke and the like and gastrointestinal disorders such as dysfunction of the gastrointestinal tract motility and, respectively, for the production of corresponding medicaments.

Furthermore, the compounds of formula

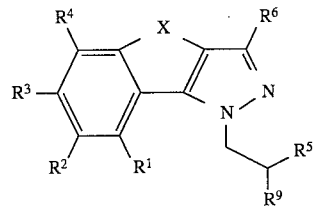

wherein $R^1$ to $R^6$ and X have the significances set forth above and $R^9$ is azido, hydroxy or a protected amino group, are an object of the invention.

The compounds of formula II are important intermediates for the manufacture of the pharmaceutically valuable compounds of formula I.

Where none of the symbols $R^1$ to $R^6$ in formula I has an asymmetric center, the compounds in accordance with the invention can be present as enantiomers, in other cases various diastereomers are possible. The invention embraces all possible stereoisomers and also mixtures thereof.

The term "lower" used in the present description denotes residues with a maximum of 7, preferably up to 4, carbon atoms, with "alkyl" denoting straight-chain, branched or cyclic saturated hydrocarbon groups such as methyl, ethyl, propyl, isopropyl or t-butyl and "alkoxy" denoting an alkyl group bonded via an oxygen atom. The term "halogen" signifies Cl, Br, F or I.

A protected amino group embrace usual protecting groups such as acetylamino or trifluoroacetylamino groups.

The term "pharmaceutically acceptable salts" embraces salts with inorganic and organic acids such as hydrochloric acid, hydrobromic acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Preferably, $R^5$ signifies lower-alkyl, methyl being especially preferred.

Especially preferred compounds in this case are those in which $R^2$ is methyl or methoxy, X is —$CH_2$— or —$C(CH_3)_2$— and $R^1$, $R^3$, $R^4$ and $R^6$ are hydrogen.

Some representative compounds defined by formula I which are particularly preferred in the scope of the present invention are:

(RS)-2-(7-Methoxy-1,4-dihydro-indeno[2,1-c]pyrazol-1-yl)-1-methyl-ethylamine fumarate (1:1), (S)-2-(7-methoxy-1,4-dihydro-indeno[2,1-c]pyrazol1-1-yl)-1-methyl-ethylamine fumarate (1:1), (S)-2-(4,4,7-trimethyl-1,4-dihydro-indeno[2,1-c]pyrazol-1-yl)-1-methyl-ethylamine fumarate (1:1), (S)-2-(7-methoxy-4,4-dimethyl-1,4-dihydro-indeno[2,1-c]-pyrazol-1-yl)-1-methyl-ethylamine fumarate (1:1), (RS)-2-(7-methoxy-4,4-dimethyl-1,4-dihydro-indenol[2,1-c]-pyrazol-1-yl)-1-methyl-ethylamine fumarate (1:1), (RS)-2-(7-ethoxy-1,4-dihydro-indeno[2,1-c]pyrazol-1-yl)-1-methyl-ethylamine fumarate (1:1);

(R)-2-(7-methoxy-1,4-dihydro-indeno[2,1-c]pyrazol-1-yl)-1-methyl-ethylamine fumarate (1:1) and (RS)-2-(8-methoxy-1-H-benz[g]indazol-1-yl)-1-methyl-ethylamine fumarate (1:0.5).

The compounds of formula I, as well as their pharmaceutically acceptable salts, can be manufactured in accordance with the invention by a) converting a compound of the formula

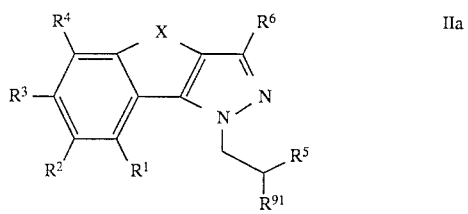

wherein $R^1$ to $R^6$ and X have the significance given above and $R^{91}$ is a group convertible into an amino group, into a corresponding amino compound and b) if desired, converting the compound of formula I obtained into a pharmaceutically acceptable salt.

The compounds of formula IIa in which $R^{91}$ is a group convertible into an amino group, preferably an azido group, an acetylamino group or another protected amino group, can be prepared according to known methods as described in more detail below.

When $R^{91}$ is an azido group, the compounds of formula I are manufactured by reduction. This can be carried out in a known manner with complex hydrides such as, for example, lithium aluminium hydride or by catalytic hydrogenation on metal catalysts such as, for example, platinum or palladium. When lithium aluminium hydride is used as the reducing agent, anhydrous ether or tetrahydrofuran is especially suitable as the solvent.

The catalytic hydrogenation on metal catalysts, for example, platinum or palladium, is conveniently effected at room temperature. Especially suitable solvents for this are: water, alcohols, ethyl acetate, dioxan or a mixture of these solvents. The hydrogenation is effected under a hydrogen atmosphere either in an autoclave or in a shaking apparatus.

When $R^{91}$ is an acetylamino group or another protected amino group such as, for example, trifluoroacetylamino, the conversion into the corresponding amino compound is effected by hydrolysis.

The hydrolysis to the corresponding amino compounds of formula I is effected according to known methods. For this there are suitable metal hydroxides, for example sodium or potassium hydroxide, which hydrolyse to the compounds of formula I in the presence of water and a water-miscible organic solvent such as an alcohol, ethylene glycol or the like.

The conversion of the compounds of formula I into their acid addition salts is effected after the hydrogenation or hydrolysis to the compounds of formula I.

The fumarates are especially well suited for pharmaceutical use because of their stability. However, all other acids mentioned in the description form pharmaceutically acceptable salts. The salt formation is effected at room temperature according to methods which will be familiar to may person skilled in the art, with alcohol-ether mixtures being especially suitable as the solvent.

The preparation of the starting materials of formula II which are required for the manufacture of the compounds of formula I is set forth in Schemes 1 and 2.

In these Schemes all substituents $R^1$ to $R^5$ have the significances given in formula I, $R^{61}$ is hydrogen or lower alkyl and Me is methyl. $X^1$ has the significance given in formula I for X, except for compounds with X=—CH=CH—, the preparation of which is shown in Scheme 3.

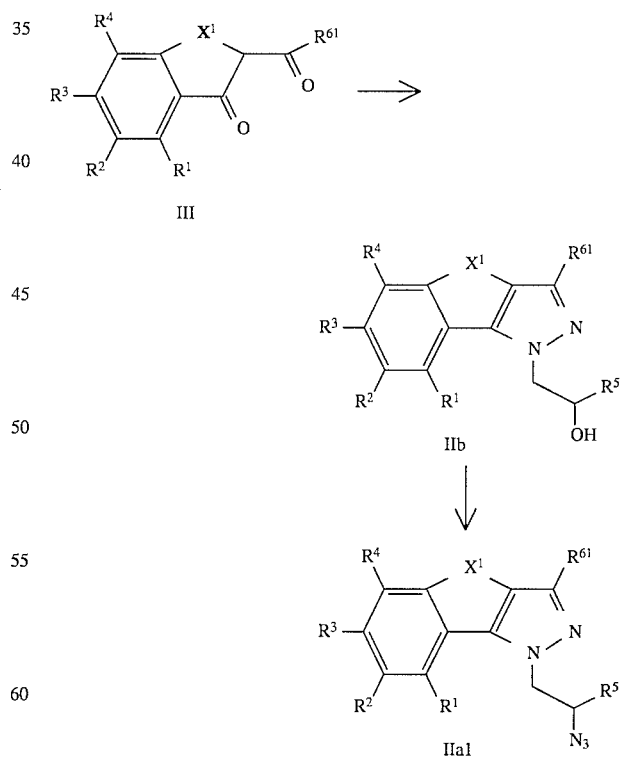

Scheme 1 shows the preparation of compounds of formula IIa1 in which $R^{61}$ is hydrogen or lower alkyl and all other substituents have the significance set forth above with the exception of X=—CH=CH—.

As set forth in Scheme I, a compound of formula III, which is known or which can be prepared by a known procedure, is converted into the corresponding pyrazole compound of formula IIb with 1-hydrazino-2-propanol and p-toluenesulfonic acid in anhydrous toluene on a water separator. Subsequently, the hydroxy group can be converted into a leaving group according to known methods, for example by reaction with a sulfonyl chloride, preferably methanesulfonyl chloride, to the sulfonate. Compounds of formula IIb1 can be converted by treatment with an azide, preferably with sodium azide, in a polar solvent, for example, dimethylformamide, into the corresponding azido compounds of formula IIa1, which, as described, can be converted into the compounds of formula I in accordance with the invention by reduction of the azido group.

Scheme 2

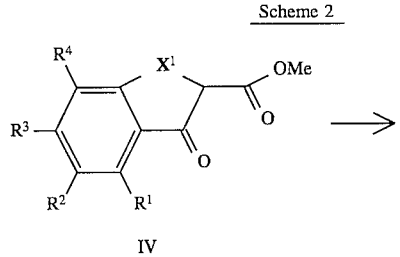

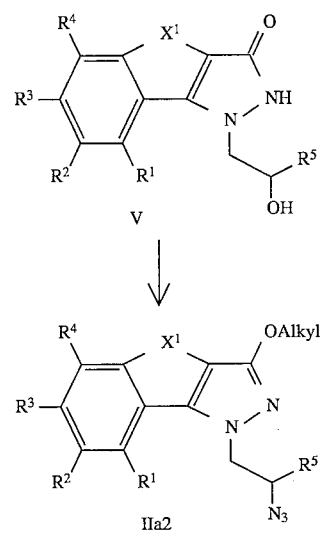

Scheme 2 shows the preparation of compounds of formula IIa2 in which the substituents $R^1$ to $R^5$ and X have the significance described above with the exception of X=—CH=CH—.

As set forth in Scheme 2, a compound of formula IV, which is known in the literature or which can be prepared by a known procedure, is conveniently converted with 1-hydrazino-2-propanol as described above into a compound of formula V. Subsequently, this compound is alkylated in an anhydrous solvent. Dialkyl sulfates or diazomethane can preferably be used as the alkylating agent. Subsequently, the OH group of the compound V can be converted according to the methods described above into a leaving group and then replaced by an azido group.

Scheme 3 hereinafter shows the manufacture of the compounds of formula Ib in which the substituents $R^1$ to $R^6$ have the significance set forth above.

Scheme 3

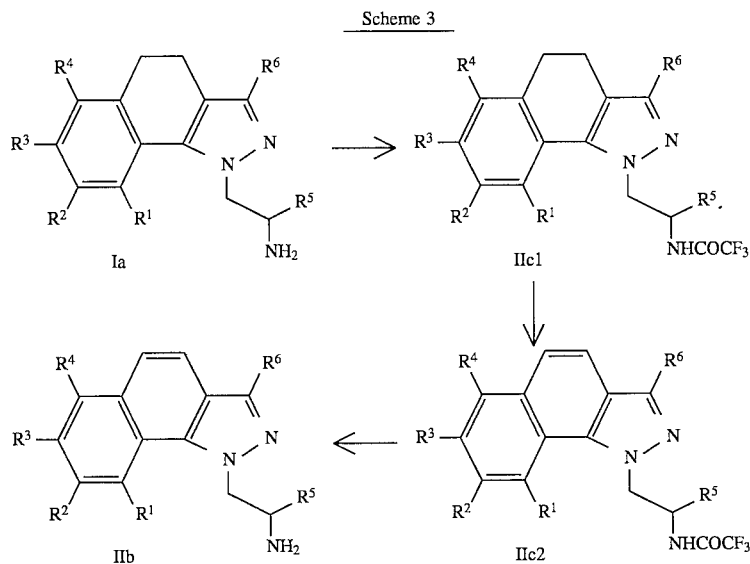

The following procedure is conveniently used:

A compound of formula Ia is reacted in a solution consisting of triethylamine and ethyl trifluoroacetate in an anhydrous solvent, preferably methanol. After removing the solvent, the residue is taken up in dioxan, treated with DDQ (2,3-dichloro-5,6 -dicyano-benzoquinone) and refluxed. After this dehydrogenation, the protecting group can be cleaved off from the amino group as described. The amino protecting group —COCF$_3$ is especially well suited in this reaction, but other protecting groups can also be used.

As mentioned earlier, the compounds of formula I and their pharmaceutically acceptable salts possess valuable pharmacological properties. They have the capacity to bind to serotonin receptors and are accordingly suitable for the treatment or prevention of illnesses or disorders of the kind referred to earlier particularly in the control of central nervous system disorders and, respectively, for the production of corresponding medicaments. In particular, the compounds of formula I are useful in treating depression.

The binding of compounds of formula I in accordance with the invention to serotonin receptors was determined in vitro by standard methods. The compounds were investigated in accordance with the assays given hereinafter:

a) Displacement assays with [3H]-5-HT(1 nM) as the radioligand on recombinant human-5HT$_{1A}$ receptors expressed in 3T3 cells of mice were carried out in order to determine the affinity of a compound to the 5HT$_{1A}$ receptor. Membranes which had been obtained from 2×10$^5$ cells were used as were various concentrations of the respective test compound.

b) For the binding to the 5HT$_{2C}$ receptor in accordance with the [3H]-5-HT binding assay according to the method of S.J Peroutka et al., Brain Research 584, 191–196 (1992).

c) For the binding to the 5HT$_{2A}$ receptor in accordance with the [3H]-DOB binding assay according to the method of T. Branchek et al., Molecular Pharmacology 38, 604–609 (1990).

The $p_{ki}$ values ($p_{ki}$=–log$_{10}$ Ki) of the test substances are given. The ki value is defined by the following formula:

$$Ki = \frac{IC_{50}}{1 + \frac{[L]}{K_D}}$$

in which the IC$_{50}$ values are those concentrations of test compounds in nmol by which 50% of the receptor-bound ligands are displaced. [L] is the concentration of ligand and the K$_D$ value is the dissociation constant of the ligand.

The thus-determined activity of some compounds in accordance with the invention will be evident from the following Table:

| | Test Method | | |
|---|---|---|---|
| | a | b | c |
| 1 | 6.45 | 8.26 | 7.03 |
| 2 | 6.47 | 8.57 | 7.31 |
| 3 | 5.38 | 8.32 | 6.64 |
| 4 | 5.58 | 8.65 | 7.43 |
| 5 | 6.20 | 7.90 | 6.72 |
| 6 | 5.74 | 8.33 | 7.31 |
| 7 | 5.61 | 7.73 | 6.44 |
| 8 | 5.17 | 7.13 | 6.08 |
| 9 | 5.37 | 5.80 | 4.80 |
| 10 | 5.78 | 8.32 | 7.30 |
| 11 | 5.75 | 7.51 | 6.58 |
| 12 | 5.91 | 7.72 | 6.85 |
| 13 | 5.92 | 8.38 | 7.31 |

-continued

| | Test Method | | |
|---|---|---|---|
| | a | b | c |
| 14 | 5.63 | 6.70 | 5.81 |
| 15 | 5.89 | 8.28 | 7.09 |
| 16 | 6.70 | 8.94 | 7.60 |
| 17 |  | 7.40 | 6.68 |
| 18 | 6.00 | 8.48 | 7.31 |

1 = (RS)-2-(7-Methoxy-1,4-dihydro-indeno[2,1-c]pyrazol-1-yl)-1-methyl-ethylamine fumarate (1:1)
2 = (S)-2-(7-Methoxy-1,4-dihydro-indeno[2,1-c]pyrazol-1-yl)-1-methyl-ethylamine fumarate (1:1)
3 = (S)-2-(4,4,7-Trimethyl-1,4-dihydro-indeno[2,1-c]pyrazol-1-yl)-1-methyl-ethylamine fumarate (1:1)
4 = (S)-2-(7-Methoxy-4,4-dimethyl-1,4-dihydro-indeno [2,1-c]pyrazol-1-yl)-1-methyl-ethylamine fumarate (1:1)
5 = (RS)-2-(4,4,7-Trimethyl-1,4-dihydro-indeno[2,1-c]pyrazol-1-yl)-1-methyl-ethylamine fumarate (1:1)
6 = (RS)-2-(7-Methoxy-4,4-dimethyl-1,4-dihydro-indeno [2,1-c]pyrazol-1-yl)-1-methyl-ethylamine fumarate (1:1)

Penile erection (rats)

It has been shown that penile erection is dependent on stimulation of the 5HT$_{2C}$ receptor (see Berendsen & Broekkamp, Eur. J. Pharmacol. 135, 179–184 (1987)).

The number of penile erections was determined within 45 minutes after administration of the test substance. The ED$_{50}$ is the dose which causes 50% of these erections.

| Example No. | ED$_{50}$ (mg/kg), s.c. |
|---|---|
| 1 | 0.32 s.c./3.2 p.o. |
| 2 | 0.32 s.c./1.4 p.o. |
| 13 | 0.5 s.c./2.7 p.o. |
| 18 | 0.7 s.c./2.3 p.o. |

The compounds of formula I and the pharmaceutically acceptable acid addition salts of the compounds of formula I can be used as medicaments, for example, in the form of pharmaceutical preparations. The pharmaceutical preparations can be administered orally, for example, in the form of tablets, coated tablets, dragées, hard and soft gelatin capsules, solutions, emulsions or suspensions. The administration can, however, also be effected rectally, for example, in the form of suppositories, parenterally, for example, in the form of injection solutions, or nasally.

For the production of pharmaceutical preparations, the compounds of formula I and the pharmaceutically acceptable acid addition salts of the compounds of formula I can be processed with pharmaceutically inert, inorganic or organic carriers. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

Medicaments containing a compound of formula I or a pharmaceutically acceptable acid addition salt thereof and a therapeutically inert carrier are also an object of the present invention, as is a process for their production which comprises bringing one or more compounds of formula I and/or pharmaceutically acceptable acid addition salts thereof into a galenical administration form together with one or more therapeutically inert carriers.

In accordance with the invention, compounds of formula I, as well as their pharmaceutically acceptable acid addition salts, can be used in the treatment or prevention of central nervous disorders such as depression. The compounds of formula I can also be used for the control or treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressivity, age-related memory disorders and behavioural disorders, addiction, obesity, bulimia etc., damages of the nervous system by trauma, stroke, neurodegenerative diseases etc., cardiovascular disorders such as hypertension, thrombosis, stroke etc. and gastrointestinal disorders such as dysfunction of the gastrointestinal tract motility and, respectively, for the production of corresponding medicaments. The dosage can vary within wide limits and will, of course, be fitted to the individual requirements in each particular case. In the case of oral administration, the dosage for an adult lies in a range of about 0.01 mg per dose to about 500 mg per day of a compound of formula I or the corresponding mount of a pharmaceutically acceptable acid addition salt thereof, although the upper limit can also be exceeded when this is found to be indicated.

The following Examples illustrate the present invention in more detail. However, they are not intended to limit its scope in any manner. All temperatures are given in degrees Celsius.

EXAMPLE 1 a) A solution of 0.95 g (5 mmol) of 2-hydroxymethylene-6-methoxy-1-indanone, 0.55 g (6 mmol) of (RS)-1-hydrazino-2-propanol and 60 mg of p-toluenesulfonic acid in 60 ml of anhydrous toluene was heated on a water separator for 2 hours. After concentration in a vacuum, the reaction mixture was purified by column chromatography on silica gel (ethyl acetate/hexane 4:1). 0.9 g (74%) of (RS)-1-(7-methoxy-1,4-dihydro-indeno[2,1-c]pyrazol-1-yl)-propan-2-ol was obtained as a yellow oil which was used directly in the next reaction.

b) 0.6 ml (7.4 mmol) of methanesulfonyl chloride was added dropwise while stirring to a solution, cooled to 0° C., of 0.9 g (3.7 mmol) of (RS)-1-(7-methoxy-1,4-dihydro-indeno[2,1-c]pyrazol-1-yl)-propan-2-ol and 2 ml (14.8 mmol) of triethylamine in 40 ml of dichloromethane and the mixture was stirred at this temperature for a further 1.5 hours. The reaction mixture was subsequently diluted with 100 ml of dichloromethane, washed twice with 50 ml of saturated sodium hydrogen carbonate solution each time and the combined aqueous phases were extracted once with 50 ml of dichloromethane. The combined organic phases were washed with 50 ml of saturated sodium chloride solution, dried over magnesium sulfate and evaporated in a vacuum. The yellow oil obtained was dissolved in 40 ml of anhydrous dimethylformamide, treated with 0.48 g (7.4 mmol) of sodium azide and the reaction mixture was heated to 70° for 15 hours while stirring. After cooling, the solution was poured into 80 ml of semi-saturated sodium chloride solution and extracted twice with 80 ml of diethyl ether each time. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate/toluene 1:1). 0.87 g (87%) of (RS)-1-(2-azido-propyl)-7-methoxy-1,4-dihydro-indeno[2,1-c]pyrazole was obtained as a light yellow oil.

c) 0.85 g (3.2 mmol) of (RS)-1-(2-azido-propyl)-7-methoxy-1,4-dihydro-indeno[2,1-c]pyrazole dissolved in 50 ml of anhydrous ethanol was hydrogenated on 85 mg of platinum oxide for 2 hours. The catalyst was subsequently filtered off, rinsed with ethanol and the solvent was removed in a vacuum. The colorless oil obtained was dissolved in 70 ml of anhydrous diethyl ether, filtered and treated while stirring with a solution of 371 mg (3.2 mmol) of fumaric acid in 10 ml of methanol. The mixture was stirred at room temperature for 15 hours and the white crystals were subsequently filtered off. 0.9 g (78%) of (RS)-2-(7-methoxy-1,4-dihydro-indeno[2,1-c]pyrazol-1-yl)-1-methyl-ethylamine fumarate (1:1) with m.p. 182° was obtained.

EXAMPLE 2 a) A solution of 1.5 g (7.9 mmol) of 2-hydroxymethylene-6-methoxy-1-indanone, 0.78 g (8.6 mmol) of (R)-1-hydrazino-2-propanol and 100 mg of p-toluenesulfonic acid in 100 ml of anhydrous toluene was heated on a water separator for 1.5 hours. After concentration in a vacuum, the reaction mixture was purified by column chromatography on silica gel (ethyl acetate/hexane 4:1). 1.3 g (68%) of (R)-1-(7-methoxy-1,4-dihydro-indeno[2,1-c]pyrazol-1-yl)-propan-2-ol were obtained as a yellow solid which was used directly in the next reaction.

b) 0.85 ml (10.7 mmol) of methanesulfonyl chloride was added dropwise while stirring to a solution, cooled to 0°, of 1.3 g (5.3 mmol) of (R)-1-(7-methoxy-1,4-dihydro-indeno[2,1-c]pyrazol-1-yl)-propan-2-ol and 3.05 ml (21.4 mmol) of triethylamine in 50 ml of dichloromethane and the mixture was stirred at this temperature for a further 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 40 ml of anhydrous dimethylformamide, treated with 0.83 g (12.5 mmol) of sodium azide and the reaction mixture was heated to 70° for 15 hours while stirring. After cooling, the solution was poured into 100 ml of semi-saturated sodium chloride solution and extracted twice with 100 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (ethyl acetate/toluene 1:1). 1.3 g (90%) of (S)-1-(2- azido-propyl)-7-methoxy-1,4-dihydro-indeno[2,1-c]pyrazole were obtained as a light yellow oil.

c) 1.3 g (4.8 mmol) of (S)-1-(2-azido-propyl)-7 -methoxy-1,4-dihydro-indeno[2,1-c]pyrazole dissolved in 50 ml of anhydrous ethanol were hydrogenated over 130 mg of platinum oxide for 2 hours. The catalyst was subsequently filtered off, rinsed with ethanol and the solvent was removed in a vacuum. The colorless oil obtained was dissolved in 80 ml of anhydrous diethyl ether, filtered and treated while stirring with a solution of 560 mg (4.8 mmol) of fumaric acid in 10 ml of methanol. The mixture was stirred at room temperature for 4 hours and the white crystals were subsequently filtered off. 1.4 g (81%) of 5(S)-2-(7-methoxy-1,4 -dihydro-indeno[2,1-c]pyrazol-1-yl)-1-methyl-ethylamine fumarate ( 1:1) with m.p. 180° were obtained.

EXAMPLE 3 a) A solution of 0.7g (3.5 mmol) of 2-hydroxymethylene-3,3,6-trimethyl-1-indanone, 0.37 g (4.1 mmol) of (R)-1-hydrazino-2 -propanol and 50 mg of p-toluenesulfonic acid in 50 ml of anhydrous toluene was heated on a water separator for 2 hours. After concentration in a vacuum, the reaction mixture was purified by column chromatography on silica gel (ethyl acetate). 0.8 g (89%) of (R)-1-(4,4,7-trimethyl-1,4-dihydro-indeno[2,1-c]pyrazol-1 -yl)-propan-2-ol was obtained as a yellow oil which was used directly in the next reaction.

b) 0.5 ml (6.24 mmol) of methanesulfonyl chloride was added dropwise while stirring to a solution, cooled to 0°, of 0.8 g (3.1 mmol) of (R)-1-(4,4,7-trimethyl-1,4-dihydro-indeno[2,1-c]-pyrazol-1-yl)-propan-2-ol and 1.75 ml (12.5 mmol) of triethylamine in 50 ml of dichloromethane and the mixture was stirred at this temperature for a further 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 40 ml of anhydrous dimethylformamide, treated with 0.41 g (6.3 mmol) of sodium azide and the reaction mixture was heated to 70° for 15 hours while stirring. After cooling, the solution was poured into 100 ml of semi-saturated sodium chloride solution and extracted twice with 100 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (ethyl acetate/toluene 1:1). 0.7 g (80%) of (S)-1-(2-azido-propyl)-4,4,7 -trimethyl-1,4-dihydro-indeno[2,1-c]pyrazole was obtained as a light yellow oil.

c) 0.7 g (2.5 mmol) of (S)-1-(2-azido-propyl)-4,4,7 -trimethyl-1,4-dihydro-indeno[2,1-c]pyrazole dissolved in 50 ml of anhydrous methanol was hydrogenated over 70 mg of platinum oxide for 2 hours. The catalyst was subsequently filtered off, rinsed with ethanol and the solvent was removed in a vacuum. The colorless oil obtained was dissolved in 70 ml of anhydrous diethyl ether, filtered and treated while stirring with a solution of 290 mg (2.5 mmol) of fumaric acid in 5 ml of methanol. The mixture was stirred at room temperature for 4 hours and the white crystals were subsequently filtered off. 0.5 g (54%) of (S)-2-(4,4,7-trimethyl-1,4 -dihydro-indeno[2,1-c]pyrazol-1-yl)-1-methyl-ethylamine fumarate (1:1) with m.p. 158° was obtained.

EXAMPLE 4 a) A solution of 1.5 g (6.8 mmol) of 2-hydroxymethylene-6-methoxy-3,3-dimethyl-1-indanone, 0.74 g (8.2 mmol) of (R)-1 -hydrazino-2-propanol and 100 mg of p-toluenesulfonic acid in 100 ml of anhydrous toluene was heated on a water separator for 1.5 hours. After concentration in a vacuum, the reaction mixture was purified by column chromatography on silica gel (ethyl acetate/hexane 4:1). 1.41 g (76%) of (R)-1-(7-methoxy-4,4 -dimethyl-1,4-dihydro-indeno[2,1-c]pyrazol-1-yl)-propan-2-ol were obtained as a yellow oil which was used directly in the next reaction.

b) 0.8 ml (10.2 mmol) of methanesulfonyl chloride was added dropwise while stirring to a solution, cooled to 0°, of 1.41 g (5.2 mmol) of (R)-1-(7-methoxy-4,4-dimethyl-1,4 -dihydro-indeno[2,1-c]pyrazol-1-yl)-propan-2-ol and 2.9 ml (20.4 mmol) of triethylamine in 50 ml of dichloromethane and the mixture was stirred at this temperature for a further 1.5 hours. The reaction mixture was subsequently diluted with 150 ml of dichloromethane, washed twice with 70 ml of saturated sodium hydrogen carbonate solution each time arid the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 40 ml of anhydrous dimethylformamide, treated with 0.76 g (11.4 mmol) of sodium azide and the reaction mixture was heated to 70° for 15 hours while stirring. After cooling, the solution was poured into 100 ml of semi-saturated sodium chloride solution and extracted twice with 100 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (ethyl acetate/toluene 1:1). 1.38 g (89%) of (S)-1-(2-azido-propyl)-7 -methoxy-4,4-dimethyl-1,4-dihydro-indeno [2,1-c]pyrazole were obtained as a yellow oil.

c) 1.38 g (4.6 mmol) of (S)-1-(2-azido-propyl)-7-methoxy- 4,4-dimethyl-1,4-dihydro-indeno[2,1-c]pyrazole dissolved in 50 ml of anhydrous ethanol were hydrogenated over 140 mg of platinum oxide for 1.5 hours. The catalyst was subsequently filtered off, rinsed with ethanol and the solvent was removed in a vacuum. The colorless oil obtained was dissolved in 80 ml of anhydrous diethyl ether, filtered and treated while stirring with a solution of 534 mg (4.6 mmol) of fumaric acid in 10 ml of methanol. The mixture was stirred at room temperature for 18 hours and the white crystals were subsequently filtered off. 1.23 g (69%) of (S)-2-(7-methoxy- 4,4-dimethyl-1,4-dihydroindeno[2,1-c]pyrazol-1-yl)-1 -methyl-ethylamine fumarate (1:1) with m.p. 160°–162° were obtained.

EXAMPLE 5 a) A solution of 1.5 g (7.4 mmol) of 2-hydroxymethylene-3,3,6-trimethyl-1-indanone, 0.55 g (6.1 mmol) of (RS)-1 -hydrazino-2-propanol and 100 mg of p-toluenesulfonic acid in 100 ml of anhydrous toluene was heated on a water separator for 2 hours. After concentration in a vacuum, the reaction mixture was purified by column chromatography on silica gel (ethyl acetate/hexane 4:1). 1.6 g (84%) of (RS)-1-(4,4,7-trimethyl-1,4-dihydro-indeno[2,1-c]-pyrazol-1-yl)-propan-2-ol were obtained as a yellow oil which was used directly in the next reaction.

b) 1 ml (12.5 mmol) of methanesulfonyl chloride was added dropwise while stirring to a solution, cooled to 0°, of 1.6 g (6.2 mmol) of (RS)-1-(4,4,7-trimethyl-1,4-dihydro-indeno[2,1-c]-pyrazol-1-yl)-propan-2-ol and 3.5 ml (25 mmol) of triethylamine in 60 ml of dichloromethane and the mixture was stirred at this temperature for a further 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 60 ml of anhydrous dimethylformamide, treated with 0.81 g (12.5 mmol) of sodium azide and the reaction mixture was heated to 70° for 15 hours while stirring. After cooling, the solution was poured into 100 ml of semi-saturated sodium chloride solution and extracted twice with 100 ml of diethyl ether each time. The combined organic phases were washed once with 100 ml of water and once with 100 ml of saturated sodium chloride solution, dried over magnesium sulfate and the solution was concentrated in a vacuum. The yellow oil obtained was purified by column chromatography on silica gel (ethyl acetate/toluene 1:1). 1.1 g (63%) of (RS)-1-(2-azido-propyl)-4,4,7-trimethyl-1,4 -dihydro-indeno[2,1-c] pyrazole were obtained as a light yellow oil.

c) 1.1 g (3.9 mmol) of (RS)-1-(2-azido-propyl)-4,4,7 -trimethyl-1,4-dihydro-indeno[2,1-c]pyrazole dissolved in 60 ml of anhydrous ethanol were hydrogenated over 110 mg of platinum oxide for 3 hours. The catalyst was subsequently filtered off, rinsed with ethanol and the solvent was removed in a vacuum. The colorless oil obtained was dissolved in 150 ml of anhydrous diethyl ether, filtered and treated while stirring with a solution of 453 mg (3.9 mmol) of fumaric acid in 10 ml of methanol. The mixture was stirred at room temperature for 4 hours and the white crystals were subsequently filtered off. 1 g (69%) of (RS)-2-(4,4,7-trimethyl-1,4 -dihydroindeno[2,1-c]pyrazol-1-yl )-1-methyl-ethylamine fumarate (1:1) with m.p. 167° was obtained.

EXAMPLE 6 a) A solution of 1.5 g (6.8 mmol) of 2-hydroxymethylene-6-methoxy-3,3-dimethyl-1-indanone, 0.74 g (8.2 mmol) of (RS)-1 -hydrazino-2-propanol and 100 mg of p-toluenesulfonic acid in 100 ml of anhydrous toluene was heated on a water separator for 2 hours. After concentration in a vacuum, the reaction mixture was purified by column chromatography on silica gel (ethyl acetate/hexane 4:1). 1.4 g (75%) of (RS)-1-(7-methoxy-4,4 -dimethyl-1,4-dihydro-indeno[2,1-c]pyrazol-1-yl)-propan-2-ol were obtained as a yellow oil which was used directly in the next reaction.

b) 0.8 ml (10.2 mmol) of methanesulfonyl chloride was added dropwise while stirring to a solution, cooled to 0°, of 1.4 g (5.1 mmol) of (RS)-1-(7-methoxy-4,4-dimethyl-1,4 -dihydro-indeno[2,1-c]pyrazol-1-yl)-propan-2-ol and 2.9 ml (20.4 mmol) of triethylamine in 50 ml of dichloromethane and the mixture was stirred at this temperature for a further 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 40 ml of anhydrous dimethylformamide, treated with 0.66 g (10.2 mmol) of sodium azide and the reaction mixture was heated to 70° for 15 hours while stirring. After cooling, the solution was poured into 100 ml of semi-saturated sodium chloride solution and extracted twice with 100 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (ethyl acetate/toluene 1:1). 1.03 g (68%) of (RS)-1-(2-azido-propyl)-7 -methoxy-4,4-dimethyl-1,4-dihydro-indeno [2,1-c]pyrazole were obtained as a yellow oil.

c) 1.03 g (3.5 mmol) of (RS)-1-(2-azido-propyl)-7 -methoxy-4,4-dimethyl-1,4-dihydro-indeno[2,1-c]pyrazole dissolved in 50 ml of anhydrous ethanol were hydrogenated over 100 mg of platinum oxide for 1.5 hours. The catalyst was subsequently filtered off, rinsed with ethanol and the solvent was removed in a vacuum. The colorless oil obtained was dissolved in 80 ml of anhydrous diethyl ether, filtered and treated while stirring with a solution of 440 mg (3.5 mmol) of fumaric acid in 15 ml of methanol. The mixture was stirred at room temperature for 15 hours and the white crystals were subsequently filtered off. 0.72 g (53%) of (RS)-2-(7 -methoxy-4,4-dimethyl-1,4-dihydroindeno[2,1-c] pyrazol-1-yl)-1 -methyl-ethylamine fumarate (1:1) with m.p. 178°–180° were obtained.

EXAMPLE 7 a) A solution of 0.51 g (2.7 mmol) of 2-hydroxymethylene- 6-methoxy-1-indanone, 0.29 g (3.2 mmol) of (S)-1-hydrazino-2 -propanol and 50 mg of p-toluenesulfonic acid in 50 ml of anhydrous toluene was heated on a water separator for 2 hours. After concentration in a vacuum, the reaction mixture was purified by column chromatography on silica gel (ethyl acetate). 0.6 g (92%) of (S)-1-(7-methoxy-1,4-dihydro-indeno[2,1-c]pyrazol-1-yl)-propan-2 -ol was obtained as a yellow solid which was used directly in the next reaction.

b) 0.4 ml (4.92 mmol) of methanesulfonyl chloride was added dropwise while stirring to a solution, cooled to 0°, of 0.6 g (2.46 mmol) of (S)-1-(7-methoxy-1,4-dihydro-indeno [2,1-c]pyrazol-1-yl)-propan-2-ol and 1.4 ml (9.84 mmol) of triethylamine in 60 ml of dichloromethane and the mixture was stirred at this temperature for a further 1.5 hours. The reaction mixture was subsequently diluted with 100 ml of dichloromethane, washed twice with 50 ml of saturated sodium hydrogen carbonate solution each time and the combined aqueous phases were extracted once with 50 ml of dichloromethane. The combined organic phases were washed with 50 ml of saturated sodium chloride solution, dried over magnesium sulfate and evaporated in a vacuum. The brown oil obtained was dissolved in 40 ml of anhydrous dimethylformamide, treated with 0.32 g (4.92 mmol) of sodium azide and the reaction mixture was heated to 80° for 15 hours while stirring. After cooling, the solution was poured into 80 ml of semi-saturated sodium chloride solution and extracted twice with 80 ml of diethyl ether each time. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate/toluene 1:1). 0.5 g (75%) of (R)-1-(2-azido-propyl)-7-methoxy-1,4 -dihydro-indeno[2,1-c]pyrazole was obtained as a yellow oil.

c) 0.5 g (1.85 mmol) of (R)-1-(2-azido-propyl)-7 -methoxy-1,4-dihydro-indeno[2,1-c]pyrazole dissolved in 50 ml of anhydrous ethanol were hydrogenated over 50 mg of platinum oxide for 2 hours. The catalyst was subsequently filtered off, rinsed with ethanol and the solvent was removed in a vacuum. The colorless oil obtained was dissolved in 70 ml of anhydrous diethyl ether, filtered and treated while stirring with a solution of 215 mg( 1.85 mmol) of fumaric acid in 5 ml of methanol. The mixture was stirred at room temperature for 15 hours and the white crystals were subsequently filtered off. 0.55 g (83%) of (R)-2-(7-methoxy-1,4-dihydro-indeno[2,1-c]pyrazol-1-yl)-1-methyl-ethylamine fumarate (1:1) with m.p. 180° was obtained.

EXAMPLE 8 a) A solution of 0.9 g (4.41 mmol) of 2-acetyl-6-methoxy-1-indanone, 0.51 g (5.73 mmol) of (RS)-1-hydrazino-2-propanol and 70 mg of p-toluenesulfonic acid in 70 ml of anhydrous toluene was heated on a water separator for 2 hours. After concentration in a vacuum, the reaction mixture was purified by column chromatography on silica gel (ethyl acetate). 1.1 g (96%) of (RS)-1-(7-methoxy-3-methyl-1,4-dihydro-indeno[2,1-c]pyrazol-1-yl)-propan-2-ol were obtained as a yellow solid which was used directly in the next reaction.

b) 0.7 ml (8.52 mmol) of methanesulfonyl chloride was added dropwise while stirring to a solution, cooled to 0°, of 1.1 g (4.26 mmol) of (S)-1-(7-methoxy-3-methyl-1,4-dihydro-indeno[2,1-c]pyrazol-1-yl)-propan-2-ol and 2.4 ml (17 mmol) of triethylamine in 60 ml of dichloromethane and the mixture was stirred at this temperature for a further 1.5 hours. The reaction mixture was subsequently diluted with 130 ml of dichloromethane, washed twice with 60 ml of saturated sodium hydrogen carbonate solution each time and the combined aqueous phases were extracted once with 50 ml of dichloromethane. The combined organic phases were washed with 70 ml of saturated sodium chloride solution, dried over magnesium sulfate and evaporated in a vacuum. The brown oil obtained was dissolved in 60 ml of anhydrous dimethylformamide, treated with 0.55 g (8.46 mmol) of sodium azide and the reaction mixture was heated to 80° for 15 hours while stirring. After cooling, the solution was poured into 80 ml of semi-saturated sodium chloride solution and extracted twice with 80 ml of diethyl ether each time. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate/toluene 1:1). 1 g (83%) of (RS)-1-(2-azido-propyl)-7-methoxy-3-methyl-1,4-dihydro-indeno[2,1-c]pyrazole was obtained as a dark brown oil.

c) 1.1 g (3.88 mmol) of (RS)-1-(2-azido-propyl)-7-methoxy-3-methyl-1,4-dihydro-indeno[2,1-c]pyrazole dissolved in 60 ml of anhydrous ethanol were hydrogenated over 110 mg of platinum oxide for 2 hours. The catalyst was subsequently filtered off, rinsed with ethanol and the solvent was removed in a vacuum. The colorless oil obtained was dissolved in 120 ml of anhydrous diethyl ether, filtered and treated while stirring with a solution of 450 mg (3.88 mmol) of fumaric acid in 5 ml of methanol. The mixture was stirred at room temperature for 15 hours and the white crystals were subsequently filtered off. 1.2 g (83%) of (RS)-2-(7-methoxy-4-methyl-1,4-dihydroindeno[2,1-c]pyrazol-1-yl)-1-methyl-ethylamine fumarate (1:1) with m.p. 184° were obtained.

EXAMPLE 9 a) A solution of 4.54 g (20.6 mmol) of 2-methoxycarbonyl-6-methoxy-1-indanone, 2.3 g (25.5 mmol) of (RS)-1-hydrazino-2-propanol and 150 mg of p-toluenesulfonic acid in 150 ml of anhydrous toluene was heated on a water separator for 4 hours. After concentration in a vacuum, the reaction mixture was taken up with ethanol and the separated solid was filtered off. The filtrate was concentrated and purified by column chromatography on silica gel (dichloromethane/methanol 9:1). 2.44 g (46%) of (RS)-1-(7-methoxy-1,4-dihydro-indeno[2,1-c]pyrazol-3-on-1-yl)-propan-2-ol were obtained as a brown oil which was used directly in the next reaction.

b) A solution of 0.79 g (18.8 mmol) of diazomethane in 56 ml of anhydrous diethyl ether was added while stirring to a solution of 2.44 g (9.37 mmol) of (RS)-1-(7-methoxy-1,4-dihydro-indeno[2,1-c]pyrazol-3-on-1-yl)-propan-2-ol in 80 ml of anhydrous diethyl ether and 50 ml of anhydrous methanol. The mixture was stirred at room temperature for a further 15 hours and subsequently concentrated in a vacuum. 2.08 g (81%) of (RS)-1-(3,7-dimethoxy-1,4-dihydro-indeno[2,1-c]pyrazol-1-yl)-propan-2-ol were obtained as a brown solid which was used directly in the next reaction.

c) 1.21 ml (15.2 mmol) of methanesulfonyl chloride were added dropwise while stirring to a solution, cooled to 0% of 2.08 g (7.6 mmol) of (RS)-1-(3,7-dimethoxy-1,4-dihydro-indeno[2,1-c]-pyrazol-1-yl)-propan-2-ol and 4.3 ml (30.4 mmol) of triethylamine in 60 ml of dichloromethane and the mixture was stirred at this temperature for a further 1.5 hours. The reaction mixture was subsequently diluted with 150 ml of dichloromethane, washed twice with 110 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The brown oil obtained was dissolved in 50 ml of anhydrous dimethylformamide, treated with 1 g (15.4 mmol) of sodium azide and the reaction mixture was heated to 70° for 20 hours while stirring. After cooling, the solution was poured into 80 ml of semi-saturated sodium chloride solution and extracted twice with 80 ml of diethyl ether each time. The combined organic phases were washed once with 80 ml of water and once with 100 ml of saturated sodium chloride solution, dried over magnesium sulfate and the solution was concentrated in a vacuum. The brown oil obtained was purified by column chromatography on silica gel (ethyl acetate/toluene 1:1). 1.11 g (49%) of (RS)-1-(2-azido-propyl)-3,7-dimethoxy-1,4-dihydro-indeno[2,1-c]pyrazole were obtained as a brown oil.

d) 1.11 g (3.71 mmol) of (RS)-1-(2-azido-propyl)-3,7-dimethoxy-1,4-dihydro-indeno[2,1-c]pyrazole dissolved in 60 ml of anhydrous ethanol were hydrogenated over 110 mg of platinum oxide for 1.5 hours. The catalyst was subsequently filtered off, rinsed with ethanol and the solvent was removed in a vacuum. The colorless oil obtained was dissolved in 50 ml of anhydrous diethyl ether, filtered and treated while stirring with a solution of 430 mg (3.71 mmol) of fumaric acid in 5 ml of methanol. The mixture was stirred at room temperature for 15 hours and the beige crystals were subsequently filtered off. 0.56 g (46%) of (S)-2-(3,7-dimethoxy-1,4-dihydroindeno[2,1-c]pyrazol-1-yl)-1-methyl-ethylamine fumarate (1:05) with m.p. 209° was obtained.

EXAMPLE 10 a) A solution of 1.4 g (8.04 mmol) of 2-hydroxymethylene- 6-methyl-1-indanone, 0.87 g (9.65 mmol) of (RS)-1-hydrazino-2-propanol and 100 mg of p-toluenesulfonic acid in 100 ml of anhydrous toluene was heated on a water separator for 2 hours. After concentration in a vacuum, the reaction mixture was purified by column chromatography on silica gel (ethyl acetate/hexane 4:1). 1.7 g (93%) of (RS)-1-(7-methyl-1,4-dihydro-indeno[2,1-c]pyrazol-1-yl)-propan-2-ol were obtained as a yellow oil which was used directly in the next reaction.

b) 1.15 ml (14.8 mmol) of methanesulfonyl chloride were added dropwise while stirring to a solution, cooled to 0°, of 1.7 g (7.45 mmol) of (RS)-1-(7-methyl-1,4-dihydro-indeno [2,1-c]pyrazol-1-yl)-propan-2-ol and 4.12 ml (29.7 mmol) of triethylamine in 60 ml of dichloromethane and the mixture was stirred at this temperature for a further 1.5 hours. The reaction mixture was subsequently diluted with 100 ml of dichloromethane, washed twice with 50 ml of saturated sodium hydrogen carbonate solution each time and the combined aqueous phases were extracted once with 50 ml of dichloromethane. The combined organic phases were washed with 50 ml of saturated sodium chloride solution, dried over magnesium sulfate and evaporated in a vacuum. The yellow oil obtained was dissolved in 40 ml of anhydrous dimethylformamide, treated with 0.96 g (14.8 mmol) of sodium azide and the reaction mixture was heated to 70° for 15 hours while stirring. After cooling, the solution was poured into 100 ml of semi-saturated sodium chloride solution and extracted twice with 100 ml of diethyl ether each time. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate/toluene 1:1). 1.38 g (73%) of (RS)-1-(2-azido-propyl)-7-methyl-1,4-dihydro-indeno[2,1-c]pyrazole were obtained as a light yellow solid with m.p. 70°–72°.

c) 1.38 g (5.45 mmol) of (RS)-1-(2-azido-propyl)-7-methyl-1,4-dihydro-indeno[2,1-c]pyrazole dissolved in 60 ml of anhydrous ethanol were hydrogenated over 140 mg of platinum oxide for 2 hours. The catalyst was subsequently filtered off, rinsed with ethanol and the solvent was removed in a vacuum. The colorless oil obtained was dissolved in 80 ml of anhydrous diethyl ether, filtered and treated while stirring with a solution of 633 mg (5.45 mmol) of fumaric acid in 10 ml of methanol. The mixture was stirred at room temperature for 15 hours and the white crystals were subsequently filtered off. 1.62 g (87%) of (RS)-2-(7-methyl-1,4-dihydroindeno[2,1-c]pyrazol-1-yl )-1-methyl-ethylamine fumarate (1:1) with m.p. 205° were obtained.

EXAMPLE 11 a) A solution of 1.42 g (8.0 mmol) of 6-fluoro-2-hydroxymethylene-1-indanone, 0.87 g (9.65 mmol) of (RS)-1-hydrazino-2-propanol and 100 mg of p-toluenesulfonic acid in 100 ml of anhydrous toluene was heated on a water separator for 1.5 hours. After concentration in a vacuum, the reaction mixture was purified by column chromatography on silica gel (ethyl acetate). 1.5 g (81%) of (RS)-1-(7-fluoro-1,4-dihydro-indeno[2,1-c]pyrazol-1-yl)-propan-2-ol were obtained as a yellow solid which was used directly in the next reaction.

b) 1 ml (12.9 mmol) of methanesulfonyl chloride were added dropwise while stirring to a solution, cooled to 0°, of 1.5 g (6.46 mmol) of (RS)-1-(7-fluoro-1,4-dihydro-indeno [2,1-c]pyrazol-1-yl)-propan-2-ol and 3.6 ml (25.8 mmol) of triethylamine in 60 ml of dichloromethane and the mixture was stirred at this temperature for a further 1.5 hours. The reaction mixture was subsequently diluted with 100 ml of dichloromethane, washed twice with 50 ml of saturated sodium hydrogen carbonate solution each time and the combined aqueous phases were extracted once with 50 ml of dichloromethane. The combined organic phases were washed with 50 ml of saturated sodium chloride solution, dried over magnesium sulfate and evaporated in a vacuum. The yellow oil obtained was dissolved in 50 ml of anhydrous dimethylformamide, treated with 0.84 g (12.9 mmol) of sodium azide and the reaction mixture was heated to 90° for 5 hours while stirring. After cooling, the solution was poured into 70 ml of semi-saturated sodium chloride solution and extracted twice with 100 ml of ethyl acetate each time. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate). 1.59 g (96%) of (RS)-1-(2-azido-propyl)-7-fluoro-1,4-dihydro-indeno[ 2,1-c]pyrazole were obtained as a light yellow oil.

c) 1.59 g (6.18 mmol) of (RS)-1-(2-azido-propyl)-7-fluoro- 1,4-dihydro-indeno[2,1-c]pyrazole dissolved in 50 ml of anhydrous ethanol were hydrogenated over 160 mg of platinum oxide for 14 hours. The catalyst was subsequently filtered off, rinsed with ethanol and the solvent was removed in a vacuum. The colorless oil obtained was dissolved in 100 ml of anhydrous diethyl ether, filtered and treated while stirring with a solution of 717 mg (6.18 mmol) of fumaric acid in 10 ml of methanol. The mixture was stirred at room temperature for S hours and the white crystals were subsequently filtered off. 1.68 g (78%) of (RS)-2-(7-fluoro-1,4-dihydroindeno[2,1-c]pyrazol-1-yl)-1-methyl-ethylamine fumarate (1:1) with m.p. 168°–170° were obtained.

EXAMPLE 12 a) A solution of 1.4 g (6.8 mmol) of 6-fluoro-2-hydroxymethylene-3,3-dimethyl-1-indanone, 0.74 g (8.2 mmol) of (RS)-1-hydrazino-2-propanol and 100 mg of p-toluenesulfonic acid in 100 ml of anhydrous toluene was heated on a water separator for 2 hours. After concentration in a vacuum, the reaction mixture was purified by column chromatography on silica gel (ethyl acetate). 1.7 g (96%) of (RS)-1-(7-fluoro-4,4-dimethyl-1,4-dihydro-indeno[2,1-c] pyrazol-1-yl)-propan-2-ol were obtained as a yellow oil which was used directly in the next reaction.

b) 1 ml (13 mmol) of methanesulfonyl chloride was added dropwise while stirring to a solution, cooled to 0°, of 1.7 g (6.5 mmol) of (RS)-1-(7-fluoro-4,4-dimethyl-1,4-dihydro-indeno[2,1-c]pyrazol-1-yl)-propan-2-ol and 3.6 ml (26 mmol) of triethylamine in 60 ml of dichloromethane and the mixture was stirred at this temperature for a further 1.5 hours. The reaction S mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 40 ml of anhydrous dimethylformamide, treated with 0.85 g (13 mmol) of sodium azide and the reaction mixture was heated to 70° for 15 hours while stirring. After cooling, the solution was poured into 100 ml of semi-saturated sodium chloride solution and extracted twice with 100 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (ethyl acetate/toluene 1:1). 1.66 g (90%) of (RS)-1-(2-azido-propyl)-7-fluoro-4,4-dimethyl-1,4-dihydro-indeno[2,1-c]pyrazole were obtained as a yellow oil.

c) 1.66 g (5.82 mmol) of (RS)-1-(2-azido-propyl)-7-fluoro-4,4-dimethyl-1,4-dihydro-indeno[2,1-c]pyrazole dissolved in 80 ml of anhydrous ethanol were hydrogenated over 160 mg of platinum oxide for 1.5 hours. The catalyst was subsequently filtered off, rinsed with ethanol and the solvent was removed in a vacuum. The yellow oil obtained was dissolved in 80 ml of anhydrous diethyl ether, filtered and treated while stirring with a solution of 676 mg (5.82 mmol) of fumaric acid in 10 ml of methanol. The mixture was stirred at room temperature for 15 hours and the white crystals were subsequently filtered off. 1.81 g (83%) of (RS)-2-(7-fluoro- 4,4-dimethyl-1,4-dihydroindeno[2,1-c]pyrazol-1-yl)- 1 -methyl-ethylamine fumarate (1:1) with m.p. 144°–146° were obtained.

EXAMPLE 13 a) A solution of 1.63 g (8 mmol) of 2-hydroxymethylene-6-ethoxy-1-indanone, 0.87 g (9.65 mmol) of (RS)-1-hydrazino-2-propanol and 100 mg of p-toluenesulfonic acid in 100 ml of anhydrous toluene was heated on a water separator for 1 hour. After concentration in a vacuum, the reaction mixture was purified by column chromatography on silica gel (ethyl acetate). 2 g (97%) of (RS)-1-(7-ethoxy-1,4-dihydro-indeno[2,1-c]pyrazol-1-yl)-propan-2 -ol were obtained as a yellow solid which was used directly in the next reaction.

b) 1.2 ml (15.5 mmol) of methanesulfonyl chloride were added dropwise while stirring to a solution, cooled to 0°, of 2 g (7.7 mmol) of (RS)-1-(7-ethoxy-1,4-dihydro-indeno[2,1-c]pyrazol-1 -yl)-propan-2-ol and 4.3 ml (31 mmol) of triethylamine in 50 ml of dichloromethane and the mixture was stirred at this temperature for a further 50 minutes. The reaction mixture was subsequently diluted with 130 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 50 ml of anhydrous dimethylformamide, treated with 1 g (15.5 mmol) of sodium azide and the reaction mixture was heated to 75° for 15 hours while stirring. After cooling the solution was poured into 80 ml of semi-saturated sodium chloride solution and extracted twice with 100 ml of diethyl ether each time. The is combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate). 2.06 g (94%) of (RS)-1-(2-azido-propyl)-7-ethoxy-1,4-dihydro-indeno[2,1-c]pyrazole were obtained as a light yellow oil.

c) 2.05 g (7.2 mmol) of (RS)-1-(2-azido-propyl)-7-ethoxy- 1,4-dihydro-indeno[2,1-c]pyrazole dissolved in 50 ml of anhydrous ethanol were hydrogenated over 200 mg of platinum oxide for 1.5 hours. The catalyst was subsequently filtered off, rinsed with ethanol and the solvent was removed in a vacuum. The colorless oil obtained was dissolved in 100 ml of anhydrous diethyl ether, filtered and treated while stirring with a solution of 836 mg (7.2 mmol) of fumaric acid in 10 ml of methanol. The mixture was stirred at room temperature for 15 hours and the white crystals were subsequently filtered off. 2.35 g (87%) of (RS)-2-(7-ethoxy-1,4-dihydroindeno[2,1-c]pyrazol-1-yl)-1-methyl-ethylamine fumarate (1:1) with m.p. 191° were obtained.

EXAMPLE 14 a) A solution of 1.4 g (7.36 mmol) of 2-hydroxymethylene- 5-methoxy-1-indanone, 0.8 g (8.83 mmol) of (RS)-1-hydrazino-2-propanol and 100 mg of p-toluenesulfonic acid in 100 ml of anhydrous toluene was heated on a water separator for 1.5 hours. After concentration in a vacuum, the reaction mixture was purified by column chromatography on silica gel (ethyl acetate/hexane 4:1). 1.74 g (97%) of (RS)-1-(6-methoxy-1,4-dihydro-indeno[2,1-c]-pyrazol-1-yl)-propan-2-ol were obtained as a yellow oil which was used directly in the next reaction.

b) 1.15 ml (14.2 mmol) of methanesulfonyl chloride were added dropwise while stirring to a solution, cooled to 0°, of 1.74 g (7.12 mmol) of (RS)-1-(6-methoxy-1,4-dihydro-indeno[2,1-c]-pyrazol-1-yl)-propan-2-ol and 3.85 ml (28.5 mmol) of triethylamine in 60 ml of dichloromethane and the mixture was stirred at this temperature for a further 50 minutes. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 40 ml of anhydrous dimethylformamide, treated with 0.92 g (14.2 mmol) of sodium azide and the reaction mixture was heated to 90° for 5 hours while stirring. After cooling, the solution was poured into 80 ml of semi-saturated sodium chloride solution and extracted twice with 100 ml of diethyl ether each time. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate/toluene 1:1). 1.58 g (82%) of (RS)-1-(2-azido-propyl)-6-methoxy-1,4 -dihydro-indeno[2,1-c]pyrazole were obtained as a light yellow oil.

c) 1.58 g (5.86 mmol) of (RS)-1-(2-azido-propyl)-6-methoxy-1,4-dihydro-indeno[2,1-c]pyrazole dissolved in 50 ml of anhydrous ethanol were hydrogenated over 160 mg of platinum oxide for 2 hours. The catalyst was subsequently filtered off, rinsed with ethanol and the solvent was removed in a vacuum. The colorless oil obtained was dissolved in 80 ml of anhydrous diethyl ether, filtered and treated while stirring with a solution of 680 mg (5.86 mmol) of fumaric acid in 10 ml of methanol. The mixture was stirred at room temperature for 15 hours and the white crystals were subsequently filtered off. 1.81 g (86%) of (RS)-2-(6-methoxy-1,4-dihydroindeno[2,1-c]pyrazol-1-yl)-1-methyl-ethylamine fumarate (1:1) with m.p. 192°–194° were obtained.

EXAMPLE 15 a) A solution of 1.63 g (7.98 mmol) of 2 -hydroxymethylene-7-methoxy-1-tetralone, 0.87 g (9.65 mmol) of (RS)-1-hydrazino-2-propanol and 100 mg of p-toluenesulfonic acid in 100 ml of anhydrous toluene was heated on a water separator for 1.5 hours. After concentration in a vacuum, the reaction mixture S was purified by column chromatography on silica gel (ethyl acetate/hexane 1:1). 1.52 g (74%) of (RS)-1-(4,5-dihydro-8-methoxy-1H-benz[g]indazol-1-yl)-propan-2-ol were obtained as a yellow oil which was used directly in the next reaction.

b) 0.89 ml (11.8 mmol) of methanesulfonyl chloride was added dropwise while stirring to a solution, cooled to 0°, of 1.52 g (5.88 mmol) of (RS)-1-(4,5-dihydro-8-methoxy-1H-benz[g]indazol-1-yl)-propan-2-ol and 3.27 ml (23.5 mmol) of triethylamine in 60 ml of dichloromethane and the mixture was stirred at this temperature for a further 1.5 hours. The reaction mixture was subsequently diluted with 100 ml of dichloromethane, washed twice with 50 ml of saturated sodium hydrogen carbonate solution each time and the combined aqueous phases were extracted once with 50 ml of dichloromethane. The combined organic phases were washed with 50 ml of saturated sodium chloride solution, dried over magnesium sulfate and evaporated in a vacuum. The brown oil obtained was dissolved in 50 ml of anhydrous dimethylformamide, treated with 0.76 g (11.8 mmol) of sodium azide and the reaction mixture was heated to 85° for 15 hours while stirring. After cooling, the solution was poured into 80 ml of semi-saturated sodium chloride solution and extracted twice with 80 ml of diethyl ether each time. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (ethyl acetate/toluene 1:1). 1 g (60%) of (RS)-1-(2-azido-propyl)-4,5-dihydro-8-methoxy-1 H-benz[g]indazole was obtained as a light yellow oil.

c) 1 g (3.5 mmol) of (RS)-1-(2-azido-propyl)-4,5-dihydro-8-methoxy-1H-benz[g]indazole dissolved in 50 ml of anhydrous ethanol was hydrogenated over 100 mg of platinum oxide for 2 hours. The catalyst was subsequently filtered off, rinsed with ethanol and the solvent was removed in a vacuum. The colorless oil obtained was dissolved in 70 ml of anhydrous diethyl ether, filtered and treated while stirring with a solution of 406 mg (3.5 mmol) of fumaric acid in 10 ml of methanol. The mixture was stirred at room temperature for 15 hours and the white crystals were subsequently filtered off. 0.98 g (75%) of (RS)-2-(4,5-dihydro-8-methoxy-1 H-benz[g]indazol-1-yl)-1-methyl-ethylamine fumarate (1:1) with m.p. 174°–176° was obtained.

EXAMPLE 16 a) A solution of 0.86 g (3.34 mmol) of (RS)-2-(4,5-dihydro-8-methoxy-1H-benz[g]indazol-1-yl)-1-methyl-ethylamine, 0.56 ml (4 mmol) of triethylamine and 0.56 ml (4 mmol) of ethyl trifluoroacetate in 60 ml of anhydrous methanol was stirred at room temperature for 50 hours. After removing the solvent in a vacuum, the residue was taken up with 70 ml of anhydrous dioxan, 0.8 g (3.5 mmol) of DDQ was added and the mixture was boiled under reflux for 3 hours. Subsequently, the reaction mixture was concentrated in a vacuum and the residue was purified by column chromatography on silica gel (dichloromethane/acetone 4:1). 0.97 g (82%) of (RS)-N-[2-(8-methoxy-1H-benz[g]indazol-1-yl)-1-methyl-ethyl]-trifluoroacetamide was obtained as a pale brown solid which was used in the next reaction without further recrystallization.

b) A mixture of 0.97 g (2.76 mmol) of RS-N-[2-(8-methoxy-1H-benz[g]indazol-1-yl)-1-methyl-ethyl]-trifluoro-acetamide, 1 g (17.5 mmol) of potassium hydroxide in 3 ml of water and 50 ml of methanol was boiled under reflux for 5 hours. The reaction mixture was subsequently poured into 100 ml of 1N sodium hydroxide solution, extracted three times with 100 ml of diethyl ether each time and the combined organic phases were dried over magnesium sulfate. After concentration in a vacuum, the residue was purified by column chromatography on silica gel (dichloromethane/methanol 9:1). There was obtained 0.62 g (2.43 mmol) of a yellow oil which was dissolved in 50 ml of diethyl ether and treated while stirring with a solution of 280 mg (2.43 mmol) of fumaric acid in 5 ml of anhydrous methanol. The mixture was stirred at room temperature for a further 17 hours and the white crystals were subsequently filtered off. 640 mg (74%) of (RS)-2-(8-methoxy-1H-benz[g]indazol-1-yl)-1-methyl-ethylamine fumarate (1:0.5) with m.p. 196°–198° C. were obtained.

EXAMPLE 17 a) A solution of 1.6 g (7.83 mmol) of 2-hydroxymethylene-6-ethoxy-1-indanone, 0.85 g (9.40 mmol) of (S)-1-hydrazino-2-propanol and 70 mg of p-toluenesulfonic acid in 80 ml of anhydrous toluene was heated on a water separator for 2 hours. After concentration in a vacuum the reaction mixture was purified by column chromatography on silica gel (ethyl acetate). 1.73 g (86%) of (S)-1-(7-ethoxy-1,4-dihydro-indeno[2,1-c]pyrazol-1-yl)-propan-2-ol were obtained as a yellow solid which was used directly in the next reaction.

b) 1.01 ml (13.4 mmol) of methanesulfonyl chloride were added dropwise while stirring to a solution, cooled to 0°, of 1.73 g (6.7 mmol) of (S)-1-(7-ethoxy-1,4-dihydro-indeno[2,1-c]pyrazol-1-yl)-propan-2-ol and 3.72 ml (26.8 mmol) of triethylamine in 50 ml of dichloromethane and the mixture was stirred at this temperature for a further 90 minutes. The reaction mixture was subsequently diluted with 130 ml of dichloromethane, washed twice with 70 ml 70 of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellowish solid obtained was dissolved in 50 ml of anhydrous dimethylformamide, treated with 0.86 g (13.4 mmol) of sodium azide and the reaction mixture was heated to 90° for 16 hours while stirring. After cooling, the solution was poured into 80 ml of semi-saturated sodium chloride solution and extracted twice with 100 ml of diethyl ether each time. The combined organic phases were washed once with 80 ml of water and once with 80 ml of saturated sodium chloride solution, dried over magnesium sulfate and the solution was concentrated in a vacuum. The yellow oil obtained was purified by column chromatography on silica gel (ethyl acetate). 1.76 g (93%) of (R)-1-(2-azido-propyl)-7-ethoxy-1,4-dihydro-indeno[2,1-c]pyrazole were obtained as a light yellow solid.

c) 1.76 g (6.21 mmol) of (R)-1-(2-azido-propyl)-7-ethoxy-1,4-dihydro-indeno[2,1-c]pyrazole dissolved in 100 ml of anhydrous ethanol were hydrogenated on 180 mg of platinum oxide for 17 hours. The catalyst was subsequently filtered off, rinsed with ethanol and the solvent was removed in a vacuum. The colorless oil obtained was dissolved in 100 ml of anhydrous diethyl ether, filtered and treated while stirring with a solution of 721 mg (6.21 mmol) of fumaric acid in 10 ml of methanol. The mixture was stirred at room temperature for 15 hours and the white crystals were subsequently filtered off. 2.0 g (86%) of (R)-2-(7-ethoxy-1,4-dihydro-indeno[2,1-c]pyrazol-1-yl)-1-methyl-ethylamine fumarate (1:1) with m.p. 161° were obtained.

EXAMPLE 18 a) A solution of 0.5 g (2.45 mmol) of 2-hydroxymethylene- 6-ethoxy-1-indanone, 0.27 g (2.94 mmol) of (R)-1-hydrazino-2 -propanol and 50 mg of p-toluenesulfonic acid in 50 ml of anhydrous toluene was heated on a water separator for 1 hour. After concentration in a vacuum, the reaction mixture was purified by column chromatography on silica gel (ethyl acetate). 0.49 g (77%) of (R)-1-(7-ethoxy-1,4-dihydro-indeno[2,1-c]pyrazol-1-yl )-propan-2-ol was obtained as a yellow solid which was used directly in the next as reaction.

b) 0.29 ml (3.79 mmol) of methanesulfonyl chloride was added dropwise while stirring to a solution, cooled to 0°, of 0.49 g (1.9 mmol) of (R)-1-(7-ethoxy-1,4-dihydro-indeno [1,2-c]pyrazol-1 -yl)-propan-2-ol and 1.06 ml (7.6 mmol) of triethylamine in 30 ml of dichloromethane and the mixture was stirred at this temperature for a further 50 minutes. The reaction mixture was subsequently diluted with 100 ml of dichloromethane, washed twice with 50 ml of saturated sodium hydrogen carbonate solution each time and the combined aqueous phases were extracted once with 50 ml of dichloromethane. The combined organic phases were washed with 70 ml of saturated sodium chloride solution, dried over magnesium sulfate and evaporated in a vacuum. The yellowish solid obtained was dissolved in 25 ml of anhydrous dimethylformamide, treated with 0.25 g (3.8 mmol) of sodium azide and the reaction mixture was heated to 70° while stirring for 22 hours. After cooling, the solution was poured into 70 ml of semi-saturated sodium chloride solution and extracted twice with 70 ml of diethyl ether each time. The combined organic phases were washed once with 50 ml of water and once with 50 ml of saturated sodium chloride solution, dried over magnesium sulfate and the solution was concentrated in a vacuum. The brown oil obtained was purified by column chromatography on silica gel (ethyl acetate). 0.53 g (99%) of (S)-1 -(2-azido-propyl)-7-ethoxy-1,4-dihydro-indeno[2,1-c]pyrazole was obtained as a light yellow solid.

c) 0.53 g (1.87 mmol) of (S)-1-(2-azido-propyl)-7-ethoxy- 1,4-dihydro-indeno[2,1-c]pyrazole dissolved in 25 ml of anhydrous ethanol was hydrogenated on 55 mg of platinum oxide for 1.5 hours. The catalyst was subsequently filtered off, rinsed with ethanol and the solvent was removed in a vacuum. The colorless oil obtained was dissolved in 50 ml of anhydrous diethyl ether, filtered and treated while stirring with a solution of 217 mg (1.87 mmol) of fumaric acid in 10 ml of methanol. The mixture was stirred at room temperature for 15 hours and the white crystals were subsequently filtered off. 0.54 g (77%) of (S)-2-(7-ethoxy-1,4-dihydro-indeno[2,1-c]pyrazol-1 -yl)-1-methyl-ethylamine fumarate (1:1) with m.p. 157° was obtained.

EXAMPLE A

Tablets of the following composition can be produced in the usual manner:

|  | mg/tablet |
|---|---|
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition can be produced in the usual manner:

|  | mg/tablet |
|---|---|
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition can be produced in the usual manner:

|  | mg/tablet |
|---|---|
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatin capsules of suitable size.

I claim:

1. A compound of the formula

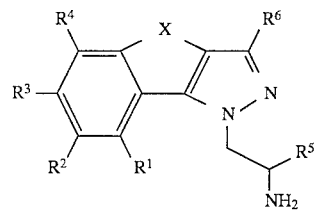

wherein $R^1$ to $R^4$ each are hydrogen, hydroxy, halogen, lower alkyl, lower alkoxy or phenyl;

$R^5$ is hydrogen or lower alkyl, $R^6$ is hydrogen, lower alkyl or lower alkoxy;

X is —(CR⁷R⁸)$_n$— or —CH=CH—;

R⁷ and R⁸ are hydrogen or lower alkyl and n is 1 or 2, or pharmaceutically acceptable salts of basic compounds of formula I.

2. The compound according to claim 1, wherein R⁵ is lower alkyl.

3. The compound of claim 2, wherein R⁵ is methyl.

4. The compound according to claim 1, wherein R² is methyl or methoxy, X is —CH$_2$— or —C(CH$_3$)$_2$— and R¹, R³, R⁴ and R⁶ are hydrogen.

5. The compound according to claim 2, wherein R² is methyl or methoxy, X is —CH$_2$— or —C(CH$_3$)$_2$— and R¹, R³, R⁴ and R⁶ are hydrogen.

6. The compound of claim 5, wherein R⁵ is methyl.

7. The compound of claim 1, (RS)-2-(7-Methoxy-1,4-dihydro-indeno[2,1-c]pyrazol-1-yl)-1-methyl-ethylamine.

8. The compound of claim 1, (S)-2-(7-Methoxy-1,4-dihydro-indeno[2,1-c]pyrazol-1-yl)-1-methyl-ethylamine.

9. The compound of claim 1, (S)-2-(4,4,7-Trimethyl-1,4-dihydro-indeno[2,1-c]-pyrazol-1-yl)-1-methyl-ethylamine.

10. The compound of claim 1, (S)-2-(7-Methoxy-4,4-dimethyl-1,4-dihydro-indeno-[2,1-c]pyrazol-1-yl)-1-methyl-ethylamine.

11. The compound of claim 1, (RS)-2-(7-Methoxy-4,4-dimethyl-1,4-dihydro-indeno-[2,1-c]pyrazol-1-yl)-1-methyl-ethylamine.

12. The compound of claim 1, (RS)-2-(7-Ethoxy-1,4-dihydro-indeno[2,1-c]pyrazol-1-yl)-1-methyl-ethylamine.

13. The compound of claim 1, (R)-2-(7-Methoxy-1,4-dihydro-indeno[2,1-c]pyrazol-1-yl)-1-methyl-ethylamine.

14. The compound of claim 1, (RS)-2-(8-Methoxy-1-H-benz[g]indazol-1-yl)-1-methyl-ethylamine.

15. A pharmaceutical composition comprising a compound of the formula

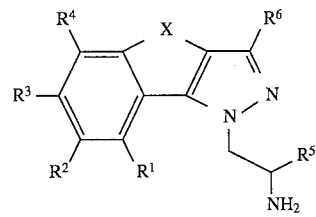

wherein

R¹ to R⁴ each are hydrogen, hydroxy, halogen, lower alkyl, lower alkoxy or phenyl;

R⁵ is hydrogen or lower alkyl,

R⁶ is hydrogen, lower alkyl or lower alkoxy;

X is —(CR⁷R⁸)$_n$— or —CH=CH—;

R⁷ and R⁸ are hydrogen or lower alkyl and n is 1 or 2, or pharmaceutically acceptable salts of basic compounds of formula I and a therapeutically inert carrier.

16. The pharmaceutical composition of claim 15, wherein in the compound of formula I, R⁵ is lower alkyl.

17. The pharmaceutical composition of claim 15, wherein in the compound of formula I, R² is methyl or methoxy, X is —CH$_2$— or —C(CH$_3$)$_2$— and R¹, R³, R⁴ and R⁶ are hydrogen.

18. The pharmaceutical composition of claim 16, wherein in the compound of formula I, R² is methyl or methoxy, X is —CH$_2$— or —C(CH$_3$)$_2$— and R¹, R³, R⁴ and R⁶ are hydrogen.

* * * * *